(12) United States Patent
Code

(10) Patent No.: US 8,257,749 B2
(45) Date of Patent: Sep. 4, 2012

(54) SYSTEMS PROVIDING AT LEAST PESTICIDAL ACTIVITY

(75) Inventor: Kenneth R. Code, Edmonton (CA)

(73) Assignee: Biolargo Life Technologies, Incorporated, Irvine, CA (US)

( * ) Notice: Subject to any disclaimer, the term of this patent is extended or adjusted under 35 U.S.C. 154(b) by 1030 days.

(21) Appl. No.: 12/012,297

(22) Filed: Jan. 31, 2008

(65) Prior Publication Data

US 2008/0193562 A1    Aug. 14, 2008

Related U.S. Application Data

(60) Provisional application No. 60/900,374, filed on Feb. 8, 2007.

(51) Int. Cl.
*A01N 59/12* (2006.01)
*A01N 25/26* (2006.01)

(52) U.S. Cl. ........ 424/667; 424/405; 424/417; 424/427; 424/490; 424/669; 424/670

(58) Field of Classification Search .................. None
See application file for complete search history.

(56) References Cited

U.S. PATENT DOCUMENTS

| | | | |
|---|---|---|---|
| 3,666,557 A | 5/1972 | Jensen et al. | 127/32 |
| 3,922,354 A | 11/1975 | Galuzzi et al. | 426/96 |
| 4,131,645 A | 12/1978 | Keblys et al. | 423/501 |
| 4,230,687 A | 10/1980 | Sair et al. | 424/485 |
| 4,375,535 A | 3/1983 | Kightlinger et al. | 527/313 |
| 4,497,930 A | 2/1985 | Yamasaki et al. | 524/556 |
| 4,731,391 A | 3/1988 | Garvey | 521/137 |
| 4,771,571 A | 9/1988 | Obrero et al. | 47/58.1 R |
| 4,888,118 A | 12/1989 | Barnes et al. | 210/668 |
| 5,162,057 A * | 11/1992 | Akiyama et al. | 106/243 |
| 5,176,836 A | 1/1993 | Sauer et al. | 210/670 |
| 5,192,546 A | 3/1993 | Abercrombie | 424/405 |
| 5,227,161 A | 7/1993 | Kessler | 424/94.4 |
| 5,246,716 A | 9/1993 | Sedun et al. | 424/713 |
| 5,346,698 A | 9/1994 | Abercrombie | 424/405 |
| 5,356,611 A | 10/1994 | Herkelmann et al. | 423/501 |
| 5,419,902 A | 5/1995 | Kessler | 424/94.4 |
| 5,464,603 A | 11/1995 | Marchin et al. | 423/501 |
| 5,629,024 A | 5/1997 | Kessler et al. | 424/667 |
| 5,639,452 A | 6/1997 | Messier | 424/78.1 |
| 5,639,481 A | 6/1997 | Kessler et al. | 424/667 |
| 5,648,075 A | 7/1997 | Kessler et al. | 424/94.4 |
| 5,674,897 A | 10/1997 | Kim et al. | 514/552 |
| 5,698,592 A | 12/1997 | Kim et al. | 514/552 |
| 5,772,971 A | 6/1998 | Murphy et al. | 422/292 |
| 5,849,291 A | 12/1998 | Kessler | 424/94.4 |
| 5,885,592 A | 3/1999 | Duan et al. | 424/400 |
| 5,919,374 A | 7/1999 | Harvey et al. | 210/753 |
| 5,962,029 A | 10/1999 | Duan et al. | 424/613 |
| 5,997,945 A | 12/1999 | Shasha et al. | 427/213.3 |
| 6,004,465 A | 12/1999 | Uhr et al. | 210/651 |
| 6,124,359 A | 9/2000 | Feitelson et al. | 514/552 |
| 6,139,731 A | 10/2000 | Harvey et al. | 210/175 |
| 6,248,335 B1 | 6/2001 | Duan et al. | 424/400 |
| 6,261,577 B1 | 7/2001 | Kessler | 424/401 |
| 6,403,674 B1 | 6/2002 | Schubert | 522/167 |
| 6,432,426 B2 | 8/2002 | Kessler | 424/401 |
| 6,875,727 B2 | 4/2005 | Hofer et al. | 504/100 |
| 7,019,036 B2 | 3/2006 | Hiromoto | 514/775 |
| 2001/0019728 A1* | 9/2001 | Basinger et al. | 424/667 |

FOREIGN PATENT DOCUMENTS

| | | | |
|---|---|---|---|
| JP | 10130014 A | * | 5/1998 |
| WO | WO85/04074 | | 3/1985 |
| WO | WO 01/74161 | | 4/2001 |
| WO | WO02058748 | | 8/2002 |

OTHER PUBLICATIONS

Periodic Table of the Elements, Los Almos National Labs, Chemistry Division (Dec. 15, 2003), "Iodine".*
The Merck Index (11th Ed. 1989), p. 414.*
P. Kapur and M. Verma, "Determination of Iodate Ion in Presence of Cupric Ion", Industrial and Engineering Chemistry Analytical Ed.: vol. 13, No. 5 (May 1941) p. 338.

* cited by examiner

*Primary Examiner* — Johann Richter
*Assistant Examiner* — Frank Choi
(74) *Attorney, Agent, or Firm* — Mark A. Litman and Associates, P.A.

(57) ABSTRACT

A process reduces the insect, arthropod or pest content in land mass by providing molecular iodine in the land mass in a concentration in aqueous material in the land mass of at least 10 parts per million. The molecular iodine may be added in gaseous or liquid or solid state, and may be formed in situ in the land mass using available water in the reaction.

18 Claims, No Drawings

SYSTEMS PROVIDING AT LEAST PESTICIDAL ACTIVITY

This application claims priority from U.S. Provisional Application 60/900,374 filed 8 Feb. 2007.

BACKGROUND OF THE INVENTION

1. Field of the Invention

The present technology relates to the field of pesticidal protection, particularly activity in soil environments that need to be protected from or cleansed of pests that might be of concern. These treatments include delivery of active ingredients and delayed activity ingredients.

2. Background of the Art

The control of arthropod pests is extremely important in achieving high crop efficiency. Arthropod damage to growing and stored agronomic crops can cause significant reduction in productivity and thereby result in increased costs to the consumer. The control of arthropod pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved as very successful parasites of both plants and animals and are responsible for significant economic losses in agriculture and livestock and for morbidity and mortality in humans (Whitehead (1998) Plant Nematode Control. CAB International, New York.).

Nematode parasites of plants can inhabit all parts of plants, including roots, developing flower buds, leaves, and stems. Plant parasites are classified on the basis of their feeding habits into the broad categories, migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control of soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the US (Carter (2001) California Agriculture, 55(3):2).

Fatty acids are a class of natural compounds that have been investigated as alternatives to the toxic, non-specific organophosphate, carbamate and fumigant pesticides (Stadler et al. (1994) Planta Medica 60(2):128-132; U.S. Pat. Nos. 5,192, 546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes. In view of this general mode of action it is not surprising that fatty acids are used in a variety of pesticidal applications including as herbicides (e.g., SCYTHE by Dow Agrosciences is the C9 saturated fatty acid pelargonic acid), as bacteriacides and fungicides (U.S. Pat. Nos. 4,771,571; 5,246,716) and as insecticides (e.g., SAFER INSECTICIDAL SOAP by Safer, Inc.).

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency results in diseased livestock and companion animals (i.e., pets), as well as in stunted growth. For instance, in cattle and dairy herds, a single untreated infection with the brown stomach worm can permanently stunt an animal's ability to effectively convert feed into muscle mass or milk.

Human infections by nematodes result in significant mortality and morbidity, especially in tropical regions of Africa, Asia, and the Americas. The World Health Organization estimates 2.9 billion people are infected with parasitic nematodes. While mortality is rare in proportion to total infections (180,000 deaths annually), morbidity is tremendous and rivals tuberculosis and malaria in disability adjusted life year measurements. Examples of human parasitic nematodes include hookworm, filarial worms, and pinworms. Hookworm is the major cause of anemia in millions of children, resulting in growth retardation and impaired cognitive development. Filarial worm species invade the lymphatics, resulting in permanently swollen and deformed limbs (elephantiasis) and invade the eyes causing African Riverblindness. *Ascaris lumbricoides*, the large gut roundworm infects more than one billion people worldwide and causes malnutrition and obstructive bowl disease.

PCT application PCT/US01/10982, filed 4 Apr. 2001 and published as WO 01/74161 incorporated herein by reference and U.S. Pat. No. 7,019,036 describes pesticidal complexes that are particularly effective with regard to nematodes and penetrants that can be used for various purposes, including as components of the pesticidal compositions. The penetrant surfactant composition consists essentially of at least one linear alcohol of 7 12C which is polyalkoxylated, at least one microemulsion-enhancing component and at least anionic detergent. This penetrant composition can be used in combination with the nematocidal or pesticidal components in agriculture as well as in alternative uses such as topical formulations for pharmaceutical or veterinary use. The pesticidal compositions themselves contain, in addition to the components of the penetrant either a lipase associated with at least one $C_{16}$ $C_{20}$ monounsaturated fatty acid or ester (including vegetable oils) or a saccharide esterified to at least one monounsaturated $C_{16}$ $C_{20}$ fatty acid. These compositions, because they contain penetrants which may not be recognized as safe as they actually are, require approval from the Environmental Protection Agency in the United States in order to be sold. In addition, the above-mentioned lipase may be derived from a fungal culture, and the complexities and uncertainties of the components of such cultures prevents their being recognized as safe. It would be desirable to formulate pesticides which are composed entirely of recognized "safe" ingredients that are environmentally friendly. If desired, of course, the compositions could be mixed with penetrants such as those described in WO 01/74161 when they are applied to the soil. This publication also describes methods to use nematacides and pesticides that are applicable to the nematacides and pesticides of the invention.

U.S. Pat. No. 6,875,727 describes a method of controlling pests with macrolide compounds; more specifically A) a method of controlling pests in and on transgenic crops of useful plants, such as, for example, in crops of maize, cereals, soya beans, tomatoes, cotton, potatoes, rice and mustard, with a macrolide compound, characterized in that a pesticidal composition comprising a macrolide compound in free form or in agrochemically useful salt form and at least one auxiliary is applied to the pests or their environment, in particular to the crop plant itself; B) A method of protecting plant propagation material and plant organs formed at a later point in time from attack by pests, characterized in that a pesticide comprising, as pesticidally active compound, at least one macrolide compound as active ingredient and at least one auxiliary in close spatial proximity to, or spatially together with, planting or applying the propagation material is employed to the site of planting or sowing; C) a method of controlling wood pests and molluscs with a macrolide compound, wherein a pesticidally active amount of a pesticide comprising, as pesticidally active compound, at least one macrolide, in free form or agrochemically utilizable salt form, as active ingredient and at least one auxiliary is applied to the pests or their environment; the corresponding use of these compounds, corresponding pesticides whose active ingredient is selected from amongst these compounds, a method for the preparation and the use of these compositions, and plant propagation material which is protected in this manner from attack by pests.

U.S. Pat. No. 5,997,945 describes adherent starch particles that may be used to carry microbicides. In PCT Int. Appl. WO 85/04074, Flashinski et al. disclose two methods of preparing a starch gel matrix containing an insecticide. The insecticide is either coextruded with a dilute, aqueous dispersion of starch, or the starch is first partially cooked in an extruder prior to cold-blending with the insecticide. In either case, the product is recovered and used as an aqueous gel.

In U.S. Pat. No. 4,230,687, Sair et al. disclose the application of shearing stress, vigorous mechanical working, and heat to distribute an active agent into an enveloping matrix of chemically modified starches, gums, and proteins in the presence of a limited quantity of water. Proteins are used for slow-release matrices; modified starches are used for rapid release.

Similarly, in U.S. Pat. No. 3,922,354, Galuzzi et al. disclose the use of high-shear mixing to incorporate active agents into low-water, high-solid matrices prepared from partially gelatinized unmodified starches. Additives such as modified dextrins, mixtures of mono and diglycerides, toasted cereal solids, and coloring agents are used to control the release of active agents.

In U.S. Pat. No. 3,666,557, Jensen et al. disclose a method of using low-fat starchy materials to microencapsulate individual beadlets of sensitive materials such as vitamins and vegetable oils. Starches are prepared for encapsulation by heating at 88° C. for 30 minutes followed by passage through a homogenizer to effect disruption of granules without degradation of molecules.

SUMMARY OF THE INVENTION

Systems and materials are provided to soil environments to be treated which generate an iodine gas-rich or iodine-dissolved-in-water rich environments that can provide pesticidal activity in a controlled manner in an exposed environment or general location. The iodine environment can be provided in numerous and varied tasks and services and even in combination with other additives such as fertilizers.

An article for application, association with or attachment to an environment that is to be treated with an iodine-rich environment, including closed environments such as green houses, and open environments such as fields, lawns, parks, orchards, farm fields, greenhouses to provide at least pesticidal activity. The article and treatments may be any delivery system that can deliver the iodine-rich environment as needed to an appropriate target. The delivery may be as a gas, packets, tablets, films, powders, concentrates, liquids and the like that may be carried in fibrous supports, film supports, free-flowing, breakable, injectable, pourable or otherwise deliverable forms such as bottles, capsules, packets, powders, coated particles or the like and may comprise a water absorbent or viscosity-enhancing material; and a composition that reacts with water to produce molecular iodine. The composition is delivered to provides a local concentration of at least 10 parts per million iodine in water carried by the material when the material has 5% by weight of water present in the water absorbent with respect to the total weight of the water absorbent material or concentrations that are sufficiently concentrated in air to address antimicrobial requirements or provide sufficient chemical activity to mediate the concentration of the targeted chemical in the environment.

DETAILED DESCRIPTION OF THE INVENTION

The potential for health and agricultural risks by the presence of pests in plants and soil has been repeatedly noted in the literature. It has also become apparent that pests become resistant to complex pesticides and that the volumes and costs of most manufactured pesticides has become prohibitive. The costs involved in making genetically modified crops reduces damage to crops, but may potentially enable the pests to persist more and become more dangerous to humans and livestock.

Additionally, it has become apparent that the overuse of chemicals in agricultural environments has accelerated the frequency of appearance and rate of appearance of antibiotic resistant pest strains in soils as well as contributing to contamination. This complicates the means of treating pests in soil and makes the total removal of contaminants from soil imperative so that the resistant strains do not move into the general animal population and the human population. It is therefore an aspect of the present invention to provide systems and materials to soil environments to be treated which generate an iodine gas-rich or iodine-dissolved-in-water rich environments that can provide pesticidal activity in a controlled environment or location. The iodine environment can be provided in numerous and varied tasks and services and even in combination with other additives such as fertilizers.

One way of providing molecular iodine ($I_2$) on site with an applicator, transporting the applicator to a site to provide reactants that can readily produce molecular iodine on-site in a controllable reaction. One format of providing the molecular iodine would be through the oxidation-reduction reaction between two salts o4r compounds to produce the molecular iodine. It is a readily controlled environment where the reaction can be performed in an aqueous environment. One reaction that can effect this would be generically described as:

$$X^+Y^- + Z+I- \rightarrow X^o + Z^+Y^- + I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

$$Cu^{+2}SO_4^{-2} + K^+I^- \rightarrow Cu^o + K_2SO_4 + I_2$$

This reaction takes place readily in an aqueous environment and produces molecular iodine at a controlled rate. The reaction may be used by wetting, dispersing or dissolving the molecular iodide and allowing the iodine in the carrying material be released and carried to the site (which may be the carrying material itself, such as the fabric, clay, fibers, film etc.) penetrate the area intended to be treated. The iodine may persist for sufficient time to treat the area, particularly within a wetted material on the surface of a patient. The reaction may also be used by dispersing or mixing the two ingredients into the carrying material (e.g., the fabric, fiber, film, sheet, etc.), either with additional water provided, with water of hydration on the first reactant (e.g., $X^+Y^- \cdot nH_2O$, such as $CuSO_4 \cdot 5H_2O$) or with ambient water in the carrying material. The two reactants may be physically separated from each other before being combined for application or reaction, as in separate capsules, particle coated droplets, fibers, layers or the like. The two reactants may be provided as a solid carrier medium or separate particulate materials that separate the two reactants until they are in contact with water (as in a soluble carrier such as polyvinyl alcohol, gelatin, amylase, sugars and the like, in pellet, fiber, dust, particle or block form). At least one of the two reactants may be independently coated with a soluble/dispersible coating and the two ingredients kept in a single water-penetrable layer.

The Technology described herein is performed by applying a solid or immediately provided carrier system to a location and either applying or awaiting the presence of sufficient water on or in the carrier system to activate the ingredients and cause the gaseous iodine to form in sufficient concentration in the solid carrier to attenuate, reduce or provide pesticidal in the solid environment such as soil or bins.

A general outline of the various generic formats in which the application of materials may be performed according to the technology described herein includes at least the following and obvious variants from the following disclosure:

1. Application of Solid Separate Particulates

Each of the ingredients (e.g., most commonly provided as KI and $CuSO_4$) can be provided as separate uncoated particles. Each of the components, preferably in anhydrous or low-moisture containers would be provided to a site. The two solid particles would be injected into or plowed into, or otherwise deposited onto or into the soil or around crops in soil. Water would either be simultaneously added, subsequently added, or even deposited immediately before the application of particles, which would then react after activation (providing a reactive medium) by the water.

2. Application of Solid Coated Separate Particulates

The individual particles of each or at least one of the reagents would be coated with a material that is removed or penetrated by water, dissolving at least one component to bring the dissolved reagent into reactive contact with the other reagent. The purpose of the at least one coating is to prevent ambient moisture from causing the two reagents to react if they are stored in the same container. For example, if only the KI were coated, ambient (atmospheric) moisture would not be present in a container in sufficient amounts to dissolve KI and carry it through the coating to the other reagent. However, when both particles are deposited into the ground, application of water by spraying or precipitation would be sufficient to penetrate or remove the coating, dissolve the KI and/or the other reagent, and allow the ingredients to react. The coating on individual particles of the reagents does not need extreme strength or durability, but only needs sufficient stability to be retained on particle surfaces during transport. For this reason, even the application of silica particles that would form a somewhat porous coating on the reagents and be held to the surface by relatively weak forces (e.g., electrostatic forces, van der Waals forces, hydrogen bonding, surface tension, etc.) have been found to be sufficient. More typical porous or continuous coatings of water-soluble or water-dispersible materials, usually deposited out of non-aqueous solvents would also be desirable in the practice of this technology. Many biodegradable or even beneficial coating materials can be used for 'green' applications, such as amylase and amylopectin polymers, naturals gums and resins, low to moderate molecular weight waxes or lipids and the like.

3. Application of Active Aqueous Agent(s)

The reagents may be added to the soil in a relatively active state, with the reagents provided as solids in a liquid carrier, coated solids in a liquid carrier, or with at least one of the ingredients dissolved at the time of application. Such an active application must be done immediately after mixture of the reagents in an active medium, as the reaction is relatively fast. For example, if both materials are provided as solids, the two solids may be provided through a single chamber, dispersed into an aqueous medium, and immediately applied (e.g., sprayed, injected, plowed) into the soil so that the majority of the release of the iodine would be within the solid environment and would not be immediately released into the air.

It would also be helpful in applying such reactive mixtures (solutions, dispersions, emulsions, suspensions, etc.) if the liquid mixture also contained a thickening agent or the like to provide reduced volatility to the water, make the solution of iodine gas adhere to the soil or plants better, and provide greater persistence to the applied liquid and the formed or carried iodine gas. Polymers, gums, resins, silica, and the like are typical thickening agents that might be used.

A simple format, in considering application to agricultural fields for treatment to prevent nematodes or other ground or water-dwelling pests or for any age or stage of pest animal, would include at least the following formats:

1) Separate particulate with separate reactants may be carried in the same container;

2) particulate and separate reactants may be carried in different containers for subsequent separate or joint application;
3) particulate reactants may be carried in the same pellets in an anhydrous condition;
4) the particulate reactants may be adhered to the same or separate carrier materials such as fertilizer pellets or seeds;
5) the reactants may be carried in carrier materials dispersed throughout or partially constituting a separate carrier material;
6) capsules or microcapsules of the reactants in water-soluble or water-dispersible shells may be dispersed over the ground; and
7) a film or films (water-soluble, water-dispersible or water-leachable) may carry one or more of the reactants, with the other reactant in a location that released or carried first reactant will be placed into contact with the second reactant in the presence of water.

Other formats and process may be used as long as the presence of water on the carrier system enables the generation of gaseous molecular iodine within the carrier in sufficient concentration to act as a pesticide.

The process may use the above reaction to form the molecular iodine represented by $$XY+ZI \rightarrow X^\circ + ZY + I_2$$

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu^\circ + K_2SO_4 + I_2.$$

The process also may be performed where the two reactants are carried in a superabsorbent polymer. The solids carriers for the two reactants may also include compositions of the present that comprise superabsorbent or non-superabsorbent polymers, natural products (e.g., papers, cellulosic solids, water-insoluble porous materials which absorb or adsorb the film-forming material within the structure, water-soluble porous materials which absorb or adsorb the film-forming material within the structure, porous containers which merely slowly release a volume of the film-forming material, porous containers which both dissolve and physically release volumes of the film-forming composition through pores, and the like. In general, selection of an effective application rate can depend on habitat depth, surface debris, emergent and surface vegetation, organic matter, microbial and algal concentration, the specific target species, and the developmental stage of the target species. Superabsorbent polymers are described, by way of non-limiting examples in U.S. Pat. Nos. 6,403,674; 4,731,391. Superabsorbent polymers, including starch graft co-polymers, are known in the art. See, for example, those described in U.S. Pat. Nos. 4,375,535 and 4,497,930 (incorporated herein by reference), which have disclosed uses as adhesives, flocculants, sizes, water-retaining materials for agriculture and water-absorbing materials for sanitary materials. However, the spectrum of advantages attendant the use of superabsorbent polymers in solid and flowable terrestrial insecticidal, pesticidal or insecticidal/pesticidal delivery compositions have gone unrecognized.

The superabsorbent polymers of the present invention are synthetic organic polymers which are solid and hydrophilic, absorbing over 100 times their weight in water. These super-absorbent polymers are typically in a powder, granule, extruded, or flake form, adapted to be blended and/or agglomerated into any shape or form.

The superabsorbent polymers may be, for example, acrylamide alkali metal acrylate co-polymers; propenenitrile homo-polymers, hydrolyzed, alkali metal salts; polymers of propenamide and propenoic acid, alkali metal salts; hydrolyzed acrylonitrile co-polymers, and starch graft co-polymers and ter-polymers thereof. All of these are designed to be hydrophilic, absorbing over 100 times their weight in water. The resulting hydrophilic polymers can absorb from over one hundred to greater than about 5000, more typically around 500 to about 1,000, times their own weight in water (measured using distilled water, pH 7.5, 25, 760 mm Hg. absorption within about 30 seconds). However, the absorption or swelling capacity and absorption or swelling time typically varies with each specific superabsorbent polymer.

One class of superabsorbent polymers include combinations of a starch and organic monomers, oligomers, polymers, co-polymers or ter-polymers. They may be manufactured in a variety of ways, for example, the methods described in U.S. Pat. Nos. 4,375,535 and 4,497,930, and can be, for example, the product of grafting corn starch (amylopectin) with acrylonitrile (an acrylic monomer or oligomer). A second class of superabsorbent polymers includes combinations of acrylamide and acrylate polymers, co-polymers and ter-polymers.

The following examples are provided as prophetic descriptions of formats for delivery of technology according to the descriptions of the present invention.

Land mass, such as soil and sand, can be contaminated by pesticides in a number of manners. The most common manner of soil contamination is from improper handling or disposal of organic wastes and sewage and by animals carrying pests into the region. Excessive rainfall can also stress sewage systems, causing them to overflow and spill raw sewage carrying the pests over the land. Whatever the source of the pest contamination, the danger to vegetation and animal life can persist for extended periods of time and can severely affect both the medical and economic health of an area. It is therefore essential that methods and plans be developed that can treat a wide variety of pest contaminations, and do so in a rapid manner and at acceptable costs.

Land mass can not be moved about readily, and materials added to soil do not disperse as widely as materials added to aqueous systems. Materials added to soil for purposes of pest reduction or elimination must not persist beyond their useful life and must not contribute a contamination effect themselves.

The technology disclosed herein is based on the discovery that the provision of molecular iodine into pest contaminated land mass (e.g., soil or sand) can mediate the land mass by killing or at least reducing the concentration of the vast majority of pest that would ordinarily persist in the land mass. Additionally, because of the transient and harmless active agents used, the materials can be used to treat agricultural land with no reasonable fear of contaminating crops.

Land mass (generally soil and/or sand) may become contaminated with any variety of pests that may be harmful to vegetation or fauna that come into contact with the pests or may be harmful if carried to animals. Although nematodes are emphasized as an example of a pest, most other known pests can be similarly addressed without any substantial variation in the practice of the technology described herein. The land mass is then treated with molecular iodine in vapor or dissolved liquid form to provide a concentration in water or aqueous mass of at least about 10 parts per million, preferably at least 30 parts per square meter of soil. The molecular iodine (as opposed to iodide anion) is provided as a) a gas, b) liquid or c) provided as two reactants that form molecular iodide (s a gas or into a liquid) in the soil, either by using an aqueous carrier, water of hydration or ambient ground water. The source of molecular iodine may be topically applied, ploughed into the soil, injected into the soil as solids dispersed solids, liquids or gels, mixed into the soil, injected into the soil separately or contemporaneously with water-removable carrier layers, sprayed onto the soil, or otherwise applied where desired. Elemental iodine is a pesticidally active form of iodine that has been used as a water disinfectant for almost a century. It is also widely used as a sanitizing compound in the food processing industry. Chlorine solution (especially hypochlorites) have been widely using by growers as a sanitizing wash for many fruits and vegetables. However, the strong oxidizing effect of chlorine in water with a moderate to high organic load results in a number of different complex compounds (trihalomethanes or THM) which can become a significant environmental hazard. There are strong reasons to minimize the excessive use of chlorine in the environment.

One way of providing molecular iodine ($I_2$) on site, rather than having to find a way of transporting it to a site) is to provide reactants that can readily produce molecular iodine on-site in a controllable reaction. One format of providing the molecular iodine would be through the oxidation-reduction reaction between two salts to produce the molecular iodine. It is a readily controlled environment where the reaction can be performed in an aqueous environment. One reaction that can effect this would be generically described as:

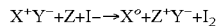

$$X^+Y^-+Z+I^-\rightarrow X^o+Z^+Y^-+I_2$$

In this reaction scheme, X is a metal (preferably a multivalent metal and more particularly a divalent metal), Y is an anion (preferably a multivalent anion and more preferably a divalent anion, and an anion having at least two oxygen atoms), Z is an alkali metal or alkaline cation. Examples of X are copper, iron, manganese, lead, nickel, tin, and the like, Y can be sulfate, sulfite, sulfonate, carbonate, phosphate, phosphate, nitrate, nitrie, borate, and the like, and Z can be sodium, lithium, potassium, ammonium, magnesium, aluminum, and the like. One preferred reaction would be:

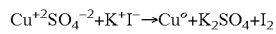

$$Cu^{+2}SO_4^{-2}+K^+I^-\rightarrow Cu^o+K_2SO_4+I_2$$

This reaction takes place readily in an aqueous environment and produces molecular iodine at a controlled rate. The reaction may be used, as intimated above, by either causing the reaction to occur in a container and directing the iodide into the soil (as by gas injection) or by dissolving the molecular iodide and injecting or spraying the dissolved iodide into or onto the soil. The reaction may also be used by dispersing or mixing the two ingredients into the land mass, either with additional water provided, with water of hydration on the first reactant (e.g., $X^+Y^-.nH_2O$, such as $CuSO_4.5H_2O$) or with ambient water in the land mass. The two reactants may be physically separated from each other before being combined for application or reaction, as in separate pouches or containers. The two reactants may be provided in a solid carrier medium that separates the two reactants until they are in contact with water (as in a soluble carrier such as polyvinyl alcohol, gelatin, amylase, sugars and the like, in pellet or block form). The two reactants may be provided as liquids in separate containers to be mixed immediately before application. The two reactants may be independently coated with a soluble/dispersible coating and the two ingredients kept in a single water-tight container.

If provided in solid form (e.g., pellets, grains, tablets, powder, blocks, etc,), the solid is preferably mixed into the soil rather than merely spread on top of the soil or sand, so as to prevent winds from blowing the solid away. If the solids are sufficiently large (e.g., at least 1.0 mm, preferably at least 2.0 mm in diameter), they can be more safely sprinkled on the surface of the soil or sand without as much concern of being blown away or unevenly distributed by the wind. The solids may be otherwise ploughed into the soil or sand, raked into the soil or sand, injected into the soil or sand, mixed with solid and sand and deposited onto the soil and sand or otherwise securely applied.

It will be apparent to one skilled in the art that there are various reactant chemicals that can be used. The reaction between anhydrous cupric sulfate and potassium iodine to produce iodine is one which is known in the art. Generally two parts (molecular stoiciometry) potassium iodine is required for every one part of anhydrous cupric sulfate to produce the desired reaction. In order to avoid problems in implementing the invention with the chemicals described above, the following matters should be noted. When using container or mixing prior to application, non-ferrous mixing containers and non-ferrous application instruments (or polymer coated ferrous material) should be used in order to avoid galvanic depositing of copper from solution. Application with absorbent and superabsorbent carriers (acrylic polymers, for example) has been found to require an additional amount of cupric sulfate over and above that used for the reaction. The reason for this is believed to be that the substrate has a tendency to sequester multivalent ions. With mixing in the vicinity of workers, care should be taken to consult safety data sheets relating to iodine gas before experimentation of any magnitude is conducted.

Soil microorganisms tend to congregate at the soil surface in a shallow layer of approximately 10 centimeters in depth. This shallow layer is referenced as either the weathering layer or the plough layer. The large majority of food (leaf fall, plant and animal detritus, etc.) is available at the soil surface. Natural biodegradation end products are fulvic and humic acids which may take up to 25-30 years to biodegrade. Microbial population size bears a direct relationship to the availability of food sources. A distribution of microorganisms may exist in the initial 75 centimeters of a soil profile and may include aerobic bacteria, anaerobic bacteria, actinomycetes, fungi, viruses, rickettsiae and algae. The total aerobic and anaerobic bacteria in the upper 8 cm of soil may be 77-80 percent of the total bacteria found in the 75 cm. profile. 95 percent of all bacteria may be found in the upper 25 cm. of the soil profile. Aerobic bacteria may average between 80-90 percent of the total bacteria for the soil horizons investigated. Thus it is desirable that the gas be provided through the major portions of this depth, e.g., at least to 8-25 centimeters.

Iodine is the preferred sanitizing agent in the food industry as it is acknowledged as a more effective user friendly sanitizing agent than chlorine. In addition, depending upon the concentrations, it is safe, can be effectively used at reduced concentrations (up to ten times less) than chlorine yet with a higher microbial kill rate. Iodine (unlike chlorine) does not produce any harmful substances such as carcinogens, and if nearly all by-products are removed, can produce an environmentally safe waste water. Being a solid at room temperatures and supplied, immersed in water, the potentially harmful effects of exposure to a concentrated sanitizing agent such as chlorine are removed, significantly improving environmental work conditions. Furthermore, iodine is less corrosive than chlorine reducing corrosive effects from the use of a biocide.

A number of United States patents disclose the use of iodine in conjunction with processes for purification of water. For example, U.S. Pat. No. 4,888,118 discloses a water purification process in which the water is passed through a mass of nylon 4 complex with iodine. The treated water is subsequently passed through nylon 4 to remove iodine from the water.

One of the difficulties with the known systems is to maintain an optimum amount of active iodine delivered into the target water supply for the specified purpose. To date there has been no effective system which can effectively and economically guarantee the delivery of exactly the right amount of active iodine at higher levels into the water used to wash produce in the case where iodine is used for food sanitization or into water delivered through reticulation networks, not only to prevent waste of iodine and economic loss but also to ensure that there is an acceptable minimum of active iodine.

Iodine recovery processes are known whose objective is to recover iodine to compensate for gradual reduction of $I_2$ in the flowing water and to provide a desired iodine residual. The process described in U.S. Pat. No. 5,176,836 is distinguished from previous systems by providing a continuous long term microbiological control process in a water supply particularly in space vehicle applications wherein $I_2$ is released into the water stream flowing through a suitable anion exchange resin.

U.S. Pat. No. 5,919,374 discloses a method and apparatus for producing bacteria free iodine species containing drinking water for farm animals under continuous dynamic water flow to produce a saturated iodine species containing aqueous solution at a pre selected temperature and blending the saturated solution with a second water flow to produce a diluted iodine species bacterium free aqueous solution.

U.S. Pat. Nos. 4,131,645; 5,356,611; 5,464,603; 5,639,452; 6,139,731; and 6,004,465 disclose prior art processes in which iodine is employed, each of which is incorporated herein by reference. The processes described in those US patents do not teach the use of means to effectively and economically control delivery of iodine in a water stream, nor do they disclose collection and conversion of iodide to iodine species for reuse in the process.

Iodinated resin beds are known as a means for recharging a water supply with a minimum amount of active iodine. The recharging is effected by treatment with an aqueous iodine solution produced by flowing water through a bed of iodine crystals. The iodine residual is monitored and the bed recharged where necessary by adjusting the flow rate of water through the bed of iodine crystals. This is an expensive method of monitoring the level of active iodine and the resin rich in bound iodine is very expensive. In addition, the capacity of the resin is limited and reloading techniques in the field would be difficult to maintain in high water flow conditions. Also, this process is best suited to low level (<4 ppm) delivery of active iodine usually in a clean filtered water environment. This is due to the slow dissolving rate of iodine from known iodine beds and the limitation of the release rate and saturation of the anion exchange resins.

An ideal level of active iodine to be maintained in the aqueous content in the soil or sand is in the range of at least or greater then 10 ppm to 25 ppm although some applications may require higher concentrations. When iodine is used in large spill sanitizing applications, it may react with organic matter in which case the active iodine can be reduced to the point where there is little left for microbiological control. If resins (e.g., superabsorbing polymers) are used to deliver active iodine, this could necessitate continual monitoring of iodine concentration. It is expensive to use resin in large areas of soil, so it is likely that this mode of delivery would be used in more localized areas. Saturation of resin with 46% weight Iodine will produce around 4 ppm active iodine release, which is insufficient alone, but with the reactive mixture, higher concentrations of molecular iodine can be provided. A controlled iodine delivery process would be one in which the level of iodine can be maintained at a predetermined optimum level and without constant manual intervention and monitoring.

The process technology of the present disclosure may be practiced in a number of formats, such as a process for reducing the pest content in land mass by providing molecular iodine in the land mass in a concentration in aqueous material in the land mass of at least 10 parts per million. The aqueous material should have a concentration of at least 10 parts per million is applied to the land mass. Specific formats include two reactants are added to the land mass and the two reactants react in the presence of water to generate a concentration of at least 10 parts per million in the water of the molecular iodine, especially where the two reactants are a) mixed with the land mass and at least some of the water present is ambient water; b) mixed with the land mass and at least some of the water present is water of hydration of one of the two reactants; c) mixed with the land mass and at least some of the water present is applied to the land mass at about the same time as the application of the two reactants; d) mixed with the land mass and at least one of the two reactants is coated to prevent premature reaction with water or another reactant. The process is particularly useful on recently contaminated sites, especially where the contaminant microbes reside in the top 25 cm of the soil such as where the land mass is sand at a site where organic waste matter has contaminated the san with microbes.

Among the ways of applying the molecular iodine are at least where molecular iodine gas is injected into the land mass; where the molecular iodine gas is generated in a closed container and injected into the land mass; where the land mass is physically disturbed to assist mixing of molecular iodine into the land mass; where physical disturbance comprises plowing of the land mass; and where solid reactant material to generate the molecular iodine is deposited in the land mass by the physical disturbance. The process may use the above reaction to form the molecular iodine represented by $$XY+ZI \rightarrow X^\circ + ZY + I_2$$

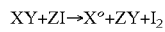

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu^\circ + K_2SO_4 + I_2.$$

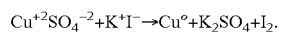

All references cited herein are incorporated by reference in their entirety.

The concentration of the iodine forming material may be selected in the article according the ultimate needs and designs of the manufacturer, and the level of ant-bacterial effect desired. The concentration of the iodine gas in the liquid in the absorbent material is one measure of the desired results, and a further measure of the desired results is referred to in the art as the kill percentage, a measure of the percent of a specific bacteria (e.g., *E. coli*) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

EXAMPLES

Example 1

In a first experiment, a natural sample from Santa Monica beach was user. This soil sample was taken from an area close to a storm drain. Concentrations started at 1100 MPN enterococci per 100 gram sediment were used. Wash samples having a concentration of greater than 10 parts per million were used on the soil samples. Enterocci concentrations approached zero for all of five consecutive washes. A longer term experiment was then performed with sand dosed with a pure culture of enterococci, the >10 ppm iodine solution imbibed in the soil, and then autoclaving. The bacterial level started at 1050 MPN/100 g, and went to zero immediately upon treatment. This was clearly evidenced in five washes (all zero). Two samples were treated with >10 ppm iodine solutions and left to sit on the roof for several days. The bacterial levels were approximately zero at the end of the experiment. Samples that were imbibed with the >10 ppm solution and the sand raked, had bacterial levels that decreased in concentration during the days, and rebounded at night for two nights, and then ended up at zero, indicating effectiveness of the solution, and a benefit to combination of the solution with heat and/or light. The undisturbed controls in both dark and light ended up with countable bacteria at the end.

Example 2

In a prophetic example, particles of KI and particles of copper sulfate are separately coated in water-removable coating materials such as silica beads ((e.g., 1-50 microns), fumed silica beads, lipids, water-softenable waxes, sugars (applied with non-aqueous solvents to avoid dissolution of the iodide or sulfate) or the like. The separate coated particles are carried to an agricultural site, the ground plowed and the particles contemporaneously sprinkled on the ground (either immediately before, during or immediately after plowing) and then watered or allowing ambient moisture or precipitation to dissolve the coating, causing generation of iodine gas or iodine dissolved in water.

Among the ways of applying the molecular iodine are at least where molecular iodine gas is injected into the land mass; where the land mass is physically disturbed to assist mixing of molecular iodine into the land mass; where physical disturbance comprises plowing of the land mass; and where solid reactant material to generate the molecular iodine is deposited in the land mass by the physical disturbance. The process may use the above reaction to form the molecular iodine represented by $$XY + ZI \rightarrow X^{oor+1} + ZY + I_2$$

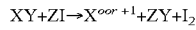

wherein X is a metal, Y is an anion, Z is an alkali metal or alkaline cation, or where X is a multivalent metal, Y is a multivalent anion, and Z is an alkali metal or alkaline cation, and is preferably represented by $$Cu^{+2}SO_4^{-2} + K^+I^- \rightarrow Cu^{oor+1} + K_2SO_4 + I_2.$$

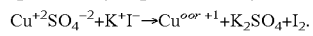

All references cited herein are incorporated by reference in their entirety.

The concentration of the iodine forming material may be selected in the article according the ultimate needs and designs of the manufacturer, and the level of anti-bacterial effect desired. The concentration of the iodine gas in the liquid in the absorbent material is one measure of the desired results, and a further measure of the desired results is referred to in the art as the kill percentage, a measure of the percent of a specific bacteria (e.g., E. coli) in a liquid sample that would be killed in 5 minutes by the level of active ingredient present. An example would be that the presence of about 8 parts per million of gaseous iodine dissolved in the aqueous material in the absorbent material would have a kill percentage over 50%. It would be desired, as noted above, to have higher concentrations of gaseous iodine in the liquid so that kill percentages are at least 60%, at least 70%, at least 80% and even at least higher than 90% for targeted bacteria and other microbes. Depending upon the specific bacteria or microbe selected for the measurement, the liquid may have to be provided with at least 5 or 10 parts per million (ppm), at least 15 ppm, at least 20 ppm, or at least 25 ppm by controlling the amount of reagents added, the rate of reaction of the reagents, and other controls aimed at keeping the iodine in solution in the liquid, such as providing thickening agents or other materials that would reduce the volatility of the iodine gas from the solution.

Example 3

In a first experiment showing the efficacy of the iodine treatment on bacteria in soil, a natural sample from Santa Monica beach was user. This soil sample was taken from an area close to a storm drain. Concentrations started at 1100 MPN enterococci per 100 gram sediment were used. Wash samples having a concentration of greater than 10 parts per million were used on the soil samples. Enterocci concentrations approached zero for all of five consecutive washes. A longer term experiment was then performed with sand dosed with a pure culture of enterococci, the >10 ppm iodine solution imbibed in the soil, and then autoclaving. The bacterial level started at 1050 MPN/100 g, and went to zero immediately upon treatment. This was clearly evidenced in five washes (all zero). Two samples were treated with >10 ppm iodine solutions and left to sit on the roof for several days. The bacterial levels were approximately zero at the end of the experiment. Samples that were imbibed with the >10 ppm solution and the sand raked, had bacterial levels that decreased in concentration during the days, and rebounded at night for two nights, and then ended up at zero, indicating effectiveness of the solution, and a benefit to combination of the solution with heat and/or light. The undisturbed controls in both dark and light ended up with countable bacteria at the end.

Example 4

Partial Prophetic

In this example, particles of KI and particles of copper sulfate are separately coated in water-removable coating materials comprising hydrophobic fumed silica (e.g., 0.1-0.5 microns, although other optional materials include cellulose fibers, lipids, water-softenable waxes, and sugars may be applied with non-aqueous solvents to avoid dissolution of the iodide or sulfate or the like. The separate coated particles might then be carried to an water drain site, the interior surface of the water drain (with biofilm deposits thereon) are pigged with a polyurethane pig under 1000 mm Hg pressure)

so that the biofilm is partially disrupted and the particles contemporaneously or subsequently dusted onto the disrupted biofilm surface of the interior of the pipe (either immediately before, during or immediately after disruption). Iodine gas and/or iodine dissolved in water would be generated at concentrations necessary for biocide applications upon the introduction of water (precipitation, direct addition, or from existing ambient moisture in the soil).

Example 5

Partial Prophetic

In a prophetic example, particles of KI were blended with 5% by weight Cab-O-Sil™ TG 709F hydrophobic fumed silica and blended together for a minimum of 30 seconds. This causes a layer of hydrophobic silica stand off particles to form a discontinuous layer on the KI surface. Old Bridge Chemicals $CuSO_4$ pentahydrate powder is also used but not treated with silica. Raw materials are mixed in the following ratio of 14.3 wt % active $CuSO_4$ and 85.7 wt % active KI. Upon intimate mixing this mixture does not show any discoloration or indication of reaction (iodine release) upon storage in 100% RH environment despite the close proximity of the intimately blended chemical reagent particles. This mixture of reagents would be carried to a water drainage system site, the biofilm coating on the interior surface of the water drainage system, rain runoff pipe disrupted and the particles contemporaneously sprayed onto the interior disrupted surface (either immediately before, during or immediately after scraping of the interior surface of the pipe along its length). Iodine gas and/or iodine dissolved in water is generated at concentrations necessary for biocide applications upon the introduction of water (precipitation, direct addition, or from existing ambient moisture in the system).

Example 6

Prophetic

A prophetic example with a rain drain system having a seventy-inch interior diameter was provided with a pigging system and pressurizing system such as those available according to the teachings of U.S. Pat. Nos. 7,000,280; 6,067,682; 5,924,158; 5,903,946; 5,384,929; and 5,265,302. The interior of the pipe surface, after being treated with such pigging systems, has at least some of the biofilm disrupted by the pigging and attendant scraping action of the pigs, so that the film is sufficiently disrupted as to readily enable penetration by liquids and gases.

Either attached to a rear end of a pig or in a trailing device (either pressure motivated or self powered (as with an electric motor robot) is a simple spraying system having a carried source of reactants and/or a feed system from an exterior source of reactants and water. For example, a single container of mixed coated particles of copper sulfate and potassium iodide can be carried in the robot and a hose providing water is connected to the robot to provide an exterior source of liquid. The solids can be fed into a mixing area and the water fed into that same mixing area, and the combination of solids (now having their coatings dissolved, which also tends to render them somewhat tacky, so as to facilitate adherence to the interior of the carrier surface) and water is sprayed onto the pipe or drain (water carrier) surface. This spraying may be done by conventional nozzles of sufficient size as to not get clogged by the carried solids and using the pressure from the water feed to spray the solution/dispersion/suspension of solids and water. It is preferred that a swiveling head be provided to assure coverage of the interior surface. It is to be noted that lower areas of the drain will be covered by runoff of liquid or the gases will disperse in the environment and contact all surfaces.

For shorter distances between the entry into the system and the points of film disruption and iodine application, it would be easy to mix materials outside of the system, transport them to the points of application, and then spray the mass without having to carry the iodine reactants themselves on the robot. By using a tackifying, slowly dissolving removable reactant coating on the particles, larger distances of application can be effected, as the reagents will adhere in the applied areas and the local presence of water will continue the iodine releasing action at the appropriate location.

Alternative disrupting means can be the hole/tunnel drilling systems with three overlapping rotating drill heads that revolve as well as rotate to provide a generally circular drilling format. The individual drill bits (e.g., the three symmetrical drill bits typically used) are also movable or adjustable radially to comport to the variations in the dimensions of the interior of the pipe and also any joints. By setting a maximum radial extension to a centimeter less than the actual minimum interior dimension of the pipe, thick biofilm can be assured of disruption without fear of causing significant damage to the pipe itself by the drill bit. Additionally, rather than the iron nitride or diamond drill bits used for tunneling, softer drill bits can be used that will abrade or disrupt the biofilm coating, but will not readily damage the pipe material.

A laser system (e.g., pulsed excimer laser may be used with the laser beam transmitted and the redirected in all directions within the interior of the drain) may also be used for physical disruption. Chemical means may be used to physically disrupt the biofilm, but reducing the chemical input into the drain is highly advantageous. Even within the present system the capture, filtering or other means of removing precipitated metals (e.g., the copper iodide) is desirable and may be required.

Example 7

Prophetic

Particles of KI would be impact coated with smaller particles (1/10 to 1/5 diameter ratio) of polyvinyl alcohol in accordance with the teachings of the processes and equipment shown in U.S. Pat. No. 6,037,019 (Kooyer). These PVA coated particles could then be mixed with particles of cupric sulfate with no concern for any immediate reaction between the salts, even in the presence of ambient moisture. These particles could be carried to the application site for admixture into water to provide iodine or into other carrier material for application to conduit surfaces. It is important to appreciate that both water-borne iodine and vapor-borne iodine can be produced in a single environment to address cracks, nooks and crannies in the delivery system where intimate contact with water might be difficult.

The activity of the materials may be increased with respect to halogen releasing ability and volume by adding further halogen releasing components, especially iodates, chlorates, bromates, periodates, perchlorates and/or perbromates as a further reagent (e.g., as above 0% to 200% by weight of the further halogen-releasing components to KI. Metal, non-metal, alkaline and alkali halogens compounds may be used.

Additional variations may be added to the system such as the application of radiation (especially Ultraviolet radiation)

in addition to the physical disruption and the iodine treatment.

All references cited herein are incorporated by reference in their entirety.

All references cited herein are incorporated by reference in their entirety.

What is claimed:

1. A process for reducing the pest content in land mass comprising providing molecular iodine into the land mass in a concentration in aqueous material in the land mass of at least 10 parts per million, the process comprising applying a composition into or onto the land mass, the composition comprising two distinct reactants as coated particles, at least one of the two reactant particles may be independently coated with a soluble/dispersible coating and the two reactants kept apart by the coating on or in the ground, and providing water on or in the ground after application of the coated particles to cause the coating to disperse or dissolve and the water carrying reactants together in or on the ground to cause the two reactants to react to form molecular iodine to attack pests in the land mass.

2. The process of claim 1 wherein an aqueous material having a concentration of at least 10 parts per million is applied to the land mass.

3. The process of claim 1 wherein the land mass has been determined to have nematodes therein as pests and the two reactants are added to the land mass and the two reactants react in the presence of water to generate a concentration of at least 10 parts per million in the water of the molecular iodine and at least some nematodes are killed by the molecular iodine.

4. The process of claim 3 wherein the two coated reactants are mixed with the land mass and at least some but less than all of the water causing the reactants to react is water present as ambient water in the ground.

5. The process of claim 3 wherein the two reactants are mixed with the land mass and at least some, but less than all of the water causing the reactants to react is water present as water of hydration of one of the two reactants.

6. The process of claim 3 wherein the two coated reactants are mixed with the land mass and at least some of the water present is applied to the land mass at about the same time as the application of the two reactants.

7. The process of claim 3 wherein the two coated reactants are mixed with the land mass and each of the two coated reactants is coated to prevent any immediate reaction between the salts in the presence of ambient moisture with the two coated reactants.

8. The process of claim 3 wherein the reaction to form the molecular iodine is represented by $XY+ZI \rightarrow X^{\circ}+ZY+I_2$ wherein X is a metal, Y is an anion, Z is an alkali metal or alkaline cation.

9. The process of claim 8 wherein the coating on particles comprises silica particles forming a porous coating on the reagents that are held to surfaces of particles.

10. The process of claim 3 wherein the reaction to form the molecular iodine is represented by $Cu_2SO_4+2K^+I^- \rightarrow 2Cu^{\circ}+2K^++SO_4^{-2}+I_2$.

11. The process of claim 3 wherein the two reactants are carried in a superabsorbent polymer.

12. The process of claim 3 wherein the coating on particles comprises silica particles forming a porous coating on the reagents that are held to surfaces of particles.

13. The process of claim 1 wherein the land mass is sand at a site where insects and/or arthropods are known to be present.

14. The process of claim 13 wherein the reaction to form the molecular iodine is represented by $XY+ZI \rightarrow X^{\circ}+ZY+I_2$ wherein, X is a multivalent metal, Y is a multivalent anion, and Z is an alkali metal or alkaline cation.

15. The process of claim 1 wherein the land mass is physically disturbed to assist mixing of molecular iodine into the land mass.

16. The process of claim 15 wherein physical disturbance comprises plowing of the land mass.

17. The process of claim 15 wherein solid reactant material to generate the molecular iodine is deposited in the land mass by the physical disturbance.

18. The process of claim 1 wherein the coating on particles comprises silica particles forming a porous coating on the reagents that are held to surfaces of particles.

* * * * *